United States Patent
Preiner et al.

(10) Patent No.: US 8,144,319 B2
(45) Date of Patent: Mar. 27, 2012

(54) AUTOMATED SOIL MEASUREMENT DEVICE

(75) Inventors: Michael John Preiner, Palo Alto, CA (US); Nicholas Carleton Koshnick, Palo Alto, CA (US); Justin Stewart White, Palo Alto, CA (US); John Paul Strachan, Millbrae, CA (US)

(73) Assignee: Solum, Inc., Mountain View, CA (US)

( * ) Notice: Subject to any disclaimer, the term of this patent is extended or adjusted under 35 U.S.C. 154(b) by 110 days.

(21) Appl. No.: 12/775,418

(22) Filed: May 6, 2010

(65) Prior Publication Data

US 2010/0283993 A1    Nov. 11, 2010

Related U.S. Application Data

(60) Provisional application No. 61/215,696, filed on May 7, 2009.

(51) Int. Cl.
    *G01N 21/01* (2006.01)
(52) U.S. Cl. ........................................ 356/244
(58) Field of Classification Search ........... 356/244–246
    See application file for complete search history.

(56) References Cited

U.S. PATENT DOCUMENTS

| | | | |
|---|---|---|---|
| 1,840,100 A | 1/1932 | Jacobsen | |
| 3,573,470 A | 4/1971 | Haley | |
| 3,861,802 A | 1/1975 | Belmear, Jr. | |
| 5,974,899 A | 11/1999 | Hanks | |
| 6,356,830 B1 | 3/2002 | Adamchuck et al. | |
| 6,596,996 B1 | 7/2003 | Stone et al. | |
| 6,931,950 B2 | 8/2005 | Malachowski et al. | |
| 6,937,939 B1 | 8/2005 | Shibusawa et al. | |
| 7,188,450 B2 | 3/2007 | Raun et al. | |
| 7,216,555 B2 | 5/2007 | Drummond et al. | |
| 2004/0009610 A1 | 1/2004 | Schabron et al. | |
| 2007/0073491 A1 | 3/2007 | Jahn et al. | |
| 2009/0166520 A1 | 7/2009 | Tuli et al. | |

OTHER PUBLICATIONS

Bouvier, J-C. et al., "On-Line Monitoring of Nitrate and Nitrite by UV Spectrophotometry in a SBR Process Used for the Treatment of Industrial Wastewaters," International Journal of Chemical Reactor Engineering, 2008, 21 pages, vol. 6.

Bravo, M. et al., "Nitrate Determination in Chilean Caliche Samples by UV-Visible Absorbance Measurements and Multivariate Calibration," J. Chil. Chem. Soc., 2009, pp. 93-98, vol. 54, No. 1.

Crumpton W.G. et al., "Nitrate and Organic N Analyses with Second-Derivative Spectroscopy," Limnol. Oceanogr., 1992, pp. 907-913, vol. 37, No. 4.

Dress, P. et al., "Water-Core Waveguide for Pollution Measurements in the Deep Ultraviolet" Applied Optics, Jul. 20, 1998, pp. 4991-4667, vol. 37, No. 21.

(Continued)

*Primary Examiner* — Michael P Stafira
(74) *Attorney, Agent, or Firm* — Fenwick & West LLP

(57) ABSTRACT

A system and a method are disclosed for combining a soil sample and extractant in a mixing chamber to produce a liquid extractant-soil mixture. A portion of the liquid extractant-soil mixture is directed from the mixing chamber through a sample measurement chamber coupled to the mixing chamber. The sample measurement chamber is coupled to a light source so that light propagates from the light source through the portion of the liquid extractant-soil mixture to an optical detector which generates an attenuation spectrum indicating light received by the detector at different wavelengths. The sample measurement chamber may include an attenuation cell having a specified optical path between a first measurement window and a second measurement window and angular surface directing particulates in the liquid extractant-soil mixture away from the attenuation cell.

20 Claims, 5 Drawing Sheets

OTHER PUBLICATIONS

Ferree, M.A. et al., "Evaluation of a Second Derivative UV/Visible Spectroscopy Technique for Nitrate and Total Nitrogen Analysis of Wastewater Samples," Wat. Res., 2001, pp. 327-332, vol. 3, No. 1.

Jannasch, H.W. et al., "The Land/Ocean Biogeochemical Observatory: A Robust Networked Mooring System for Continuously Monitoring Complex Biogeochemical Cycles in Estuaries," Limnology and Oceanography: Methods, 2008, pp. 263-276, vol. 6.

Johnson, K.S. et al., "In Situ Ultraviolet Spectrophotometry for High Resolution and Long-Term Monitoring of Nitrate, Bromide and Bisulfide in the Ocean," Deep-Sea Research Part I, 2002, pp. 1291-1305, vol. 49.

Karlsson, M. et al., "Determination of Nitrate in Municipal Waste Water by UV Spectroscopy," Analytica Chimica Acta, 1995, pp. 107-113, vol. 312.

PCT International Search Report and Written Opinion, PCT Application No. PCT/US2010/034053, Jul. 1, 2010, 9 pages.

Pruitt, P., "Nitrate Measurement in Less Than 30 Seconds," Water Environment Laboratory, Feb./Mar. 2009, pp. 1-15, vol. 16, No. 1.

Ratako, A. et al., "Micro- and Mini-Nitrate Sensors for Monitoring of Soils, Groundwater and Aquatic Systems," Center for Embedded Network Sensing, May 12, 2009, 3 pages.

Sempere, A. et al., "Simple Determination of Nitrate in Soils by Second-Derivative Spectroscopy," Journal of Soil Science, 1993, pp. 633-639, vol. 44.

Sethuramasamyraja, B. et al. Agitated soil measurement method for integrated on-the-go mapping of soil ph, potas,sium and nitrate contents. Computers and Electronics in Agriculture, 60:212-225, 2008.

Thomas, O. et al., "Ultraviolet Multiwavelength Absorptiometry (UVMA) for the Examination of Natural Waters and Wastewaters, Part I: General Considerations," Fresenius' Journal of Analytical Chemistry, 1990, pp. 234-237, vol. 338.

Thomas, O. et al., "Ultraviolet Multiwavelength Absorptiometry (UVMA) for the Examination of Natural Waters and Wastewaters, Part II. Determination of Nitrate" Fresenius' Journal of Analytical Chemistry, 1990, pp. 238-240, vol. 338.

Tuli, A. et al., "In Situ Monitoring of Soil Solution Nitrate: Proof of Concept," SSSAJ, Mar.-Apr. 2009, pp. 501-509, vol. 73, No. 2.

Yao, H. et al., "Hyperspectral Image Feature Extraction and Classification for Soil Nutrient Mapping," Precision Agriculture: Papers from the 4th European Conference on Precision Agriculture, Berlin, Germany, Jun. 15-19, 2003, p. 216.

AUTOMATED SOIL MEASUREMENT DEVICE

CROSS REFERENCE TO RELATED APPLICATIONS

This application claims the benefit of U.S. Provisional Application No. 61/215,696, filed May 7, 2009, which is incorporated by reference in its entirety.

BACKGROUND

1. Field of Art

The present invention generally relates to soil measurement and testing, and more specifically, automated measurement of soil properties.

2. Description of the Related Art

Nutrient levels in soil have significant spatial and temporal variations. Accordingly, there has been significant effort placed into development of local nutrient management schemes, often referred to as "precision agriculture," addressing nutrient level variation. Local nutrient management increases agricultural efficiency while reducing its environmental impact by allowing growers to locally apply nutrients where needed. Increases in nutrient costs and a growing awareness of the environmental consequences of current agriculture practices have made improvements in agricultural efficiency and environmental impact increasingly important.

For example, fertilizer inputs are a large fraction of agricultural input costs and prices of nutrient input have almost doubled in recent years, increasing concern about future price fluctuations among growers. Meanwhile, in addition to long-standing concerns about the effect of fertilizers on water quality, greenhouse gas emissions caused by nitrogen-based fertilizers have become an increasing concern. For example, it is estimated that $N_2O$ emissions caused by fertilizer volatilization are responsible for 5-10% of the forcing for global warming. Thus the ability to optimize the use of fertilizer inputs, and nitrogen-based fertilizers in particular, is increasingly recognized as a vital component of environmental sustainability. As a result of these factors, there is a rapidly growing interest in more efficient nutrient management.

Local measurement of soil nutrient levels is a significant component of local nutrient management scheme. However, conventional methods for locally measuring soil nutrient levels have limited the effectiveness of existing local nutrient management schemes. Conventionally, capturing a number of samples/acre at the appropriate time to make effective decisions is often prohibitively time consuming and expensive. For example, lettuce growers in certain area typically plant several crop cycles each year, and have a five day window between harvesting and planting the next crop. Logistically, this results in a very small time window, 1-2 days, in which to sample the field and apply fertilizer. This short time frame prevents use of standard laboratory-based soil testing, which often takes 1-2 weeks to provide a result. Consequently, growers typically make decisions on fertilizer application based on historical analysis, instead of on current soil conditions.

As another example, in-season nitrogen management in corn-growing regions is often difficult because of the slow turnaround time of laboratory-based soil testing. Extending the time when corn growers are able to measure soil nitrogen levels would allow corn growers to test fields before their last application of fertilizer. This enables corn growers to test fields later in the growing season and implement nitrogen management practices. Further, allowing growers to promptly retest fields, such as retesting after a rain, allows growers to adopt more efficient nitrogen management practices. Additionally, laboratory-based soil measurement costs scale directly with the number of samples, making it prohibitively expensive to sample at high grid densities. Thus, the development of a fast, simple, and inexpensive soil would expand the benefits of precision agriculture.

Nitrate-nitrogen is one of most important nutrients for a variety of crops, but it is particularly mobile in the soil, making it subject to large spatial variations. Additionally, mapping soil nitrate levels using standard laboratory-based tests is relatively slow and expensive. Accordingly, there have thus been numerous efforts to develop fast soil nitrate detection tools. Technologies used have ranged from mid-infrared (mid-IR) spectroscopy to ion-selective electrodes. However, the use of each currently developed method has suffered from some combination of expense, low accuracy, stringent calibration requirements or difficulty of use.

There have been several recent efforts to perform fast, "on-the-go" measurements of soil nitrate-nitrogen using ion-selective electrodes. While these ion-selective systems have shown the feasibility of making rapid measurements on soil-extractant mixtures, the fragility of the ion-selective membrane itself has caused significant problems with the robustness and reproducibility of soil measurements. Ion-selective systems also require frequent calibration, making them unappealing for routine field use. Nitrate "strip tests", commonly available from scientific supply stores or from manufacturers, or hand-held spectrometers have also been used. However, nitrate strip tests typically suffer from poor accuracy compared to standard laboratory-based tests and require extensive sample preparation, including consumable reagents. For example, the standard preparation time for nitrate strip tests typically approaches 30 minutes, includes numerous preparation steps and requires precise timing of the reaction steps.

Accordingly, a rapid and economical system for soil analysis could provide more accurate and timely nutrient management recommendations which improve agricultural efficiency.

SUMMARY

One embodiment of a disclosed system (and method) includes a device for processing a soil sample and analyzing the processed soil sample to identify characteristics of the soil sample. For example, a soil sample is combined with an extractant, such as water, to produce a liquid extractant-soil mixture. A portion of the liquid extractant-soil mixture is exposed to a broad-band light source, with wavelengths varying from ultraviolet to visible to near-infrared, and an attenuation spectrum identifying the attenuation of different wavelengths of the ultraviolet, visible and near infrared light by the portion of the liquid extractant-soil mixture. The attenuation spectrum is then analyzed to determine components within the soil sample. For example, peaks in the attenuation spectrum are analyzed to identify different nutrients included in the soil sample, allowing rapid identification of various nutrients within the soil sample.

In one embodiment, a mixing chamber combines a soil sample and extractant received through one or more ports. For example, the mixing chamber includes a mixing shaft which moves to combine the soil sample and extractant to produce a liquid extractant-soil mixture, although the mixing chamber may also include sonication, heating, chemical addition or another suitable method to mix the soil sample and extractant to produce the liquid extractant-soil mixture. A portion of the liquid extractant-soil mixture is directed from the mixing chamber to a sample measurement chamber. In one embodiment, the liquid extractant-soil mixture is directed through a filter before entering the sample measurement chamber to remove particulates from the portion. The sample measurement chamber is coupled to a light source so that light propagating from the light source is attenuated by the portion of the liquid extractant-soil mixture and then measured by optical detector which generates an attenuation spectrum indicating light received by the detector at different wavelengths.

In one embodiment, the sample measurement chamber includes an attenuation cell having a specified optical path between a first measurement window and a second measurement window. The sample measurement window also includes an angular surface configured to direct particulates in the liquid extractant-soil mixture away from the attenuation cell. In one embodiment, a first set of spacers of a first transmission window holder contacts a second set of spacers of a second transmission window holder to determine the optical path of the attenuation cell. Ultraviolet, visible and near-infrared light is transmitted through the first transmission window and through the portion of the liquid extractant-soil mixture included in the attenuation cell. A fraction of the ultraviolet, visible and near-infrared light passes through the portion of the liquid extractant-soil mixture included in the attenuation cell and through the second measurement window to an optical detector.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF DRAWINGS

The disclosed embodiments have other advantages and features which will be more readily apparent from the following detailed description and the appended claims, when taken in conjunction with the accompanying drawings, in which:

DETAILED DESCRIPTION

The Figures (FIGS.) and the following description relate to preferred embodiments of the present invention by way of illustration only. It should be noted that from the following discussion, alternative embodiments of the structures and methods disclosed herein will be readily recognized as viable alternatives that may be employed without departing from the principles of the claimed invention.

Reference will now be made in detail to several embodiments, examples of which are illustrated in the accompanying figures. It is noted that wherever practicable similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles described herein.

Structure of Analysis Device and Sample Measurement Chamber

Figure 1:
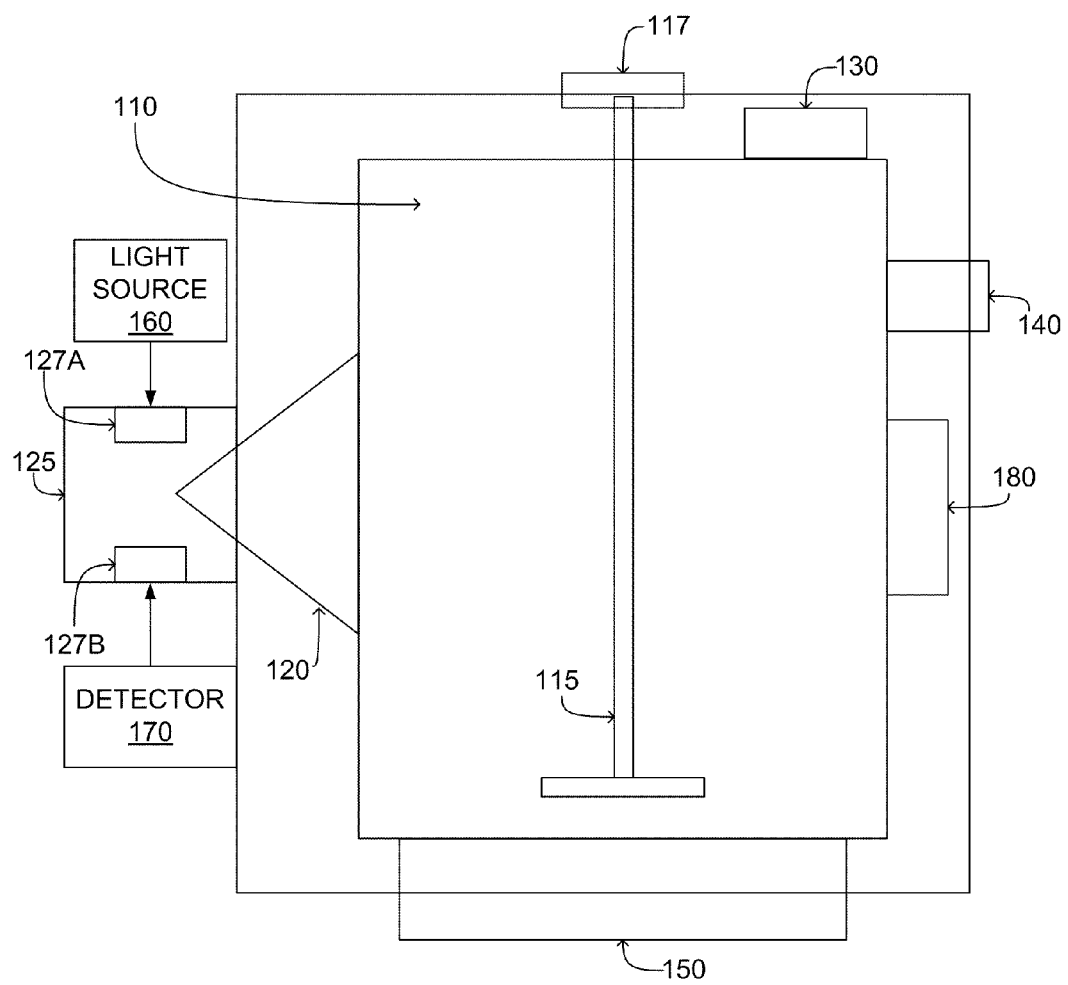
FIG. 1 is a block diagram of one embodiment of a soil analysis device for sample processing and data measurement.

FIG. 1 is a block diagram of one embodiment of a soil analysis device 100. The soil analysis device 100 includes a mixing chamber 110 having a first port 130 and a second port 140. In one embodiment, a soil sample and/or an extractant, such as water, is received by the mixing chamber 110 receives a soil sample through the first port 130. For example, the mixing chamber 110 is initially filled with a predetermined amount of extractant through the first port 130 and then receives a soil sample through the first port 130. Alternatively, the mixing chamber 110 initially receives a soil sample through the first port 130 and then receives extractant through the first port 130. In another configuration, the mixing chamber 110 receives a soil sample through the first port 130 and receives extractant through the second port 140. Soil samples may be manually provided to the mixing chamber 110 through the first port 130 or may automatically be provide to the mixing chamber 110 through the first port 130 by a soil supply device or other device. In one configuration where water is used as the extractant, after receiving the soil sample, the first port 130 is coupled to a supply of additional extractant, allowing the extractant to soil ratio in the mixing chamber 110 to be modified by addition of extractant through the first port 130. This ability to dynamically dilute the soil sample enables the soil analysis device 100 to perform a variety of soil analyses spanning multiple soil-to-water, or soil-to-extractant ratios. For example, the mixing chamber 110 may initially have a 1:20 soil-to-extractant ratio, and after analyzing the soil sample, additional extractant may be provided so that the soil-to-extractant ratio is becomes 1:50, allowing additional data about the soil sample to be captured by a different analysis.

In one embodiment, a soil sample is automatically or manually weighed before being inserted into the mixing chamber 110 through the first port 130. Determining the weight of a soil sample before mixing allows more accurate determination of the concentration of soil nutrients measured by one or more sample measurement chambers 125, further described below. Additionally, the extractant added to the mixing chamber 110 through the first port 130 has a determined volume or weight to improve the accuracy of subsequent measurements.

In one embodiment, the second port 140 directs additional chemicals into the mixing chamber 110, allowing the mixing chamber to combine the additional chemicals with a soil sample and extractant. For example, the second port 140 directs an additional soil extractant into the mixing chamber along with water, which then mixes the additional soil extractant with a received soil sample and water, allowing the mixing chamber 110 to provide data about the composition or characteristics of the soil sample. As another example, the second port 140 may direct a pH indicator such as litmus or phenol red into the mixing chamber 110. The second port 140 may direct solid chemicals, such as capsules, or liquid chemicals from an external tank or supply into the mixing chamber 110. Note that in various configurations, either the first port 130 or the second port 140 may be used to provide soil, water, extractant and/or chemicals to the mixing chamber 110, allowing the soil analysis device 100 to operate in a range of orientations and operating environments.

In the example configuration shown by FIG. 1, the mixing chamber 110 includes a mixing shaft 115 coupled to a motor 117, which mixes together the contents of the mixing chamber 110. For example, the mixing shaft 115 produces an extractant-soil mixture by agitating the extractant and a soil sample included in the mixing chamber 110. The mixing shaft 115 may also combine additional chemicals with the extractant and a soil sample included in the mixing chamber 110 when producing the extractant-soil mixture. For purposes of illustration, FIG. 1 depicts an embodiment where the mixing shaft 115 enters the mixing chamber 110 from an opening on the top of the mixing chamber 115; however, in other embodiments, the mixing shaft 115 enters the mixing chamber 110 from an opening on the bottom or side of the mixing chamber 110. Additionally, in other embodiments, the mixing chamber 110 may use any suitable method for mixing the contents of the mixing chamber. For example, the mixing chamber may use one or more of sonication, heating or chemical addition, or any other method of mixing or combinations of methods of mixing to combine the contents of the mixing chamber 110. As another example, the mixing chamber 110 may include one or more blades which are moved by the motor 117, or another power source, to combine a soil sample and an extractant.

The mixing chamber 110 also includes an outlet port 150 allowing removal of the contents of the mixing chamber 110. For example, the outlet port 150 is an opening having a movable cover, so that moving the cover allows drainage of the contents of the mixing chamber 110. Additionally, the outlet port 150 may also be used to apply heat to the contents of the mixing chamber 110. For example, the outlet port 150 is heated by a heat source, allowing the outlet port 150 to radiate the received heat to the mixing chamber 110.

Figure 2:
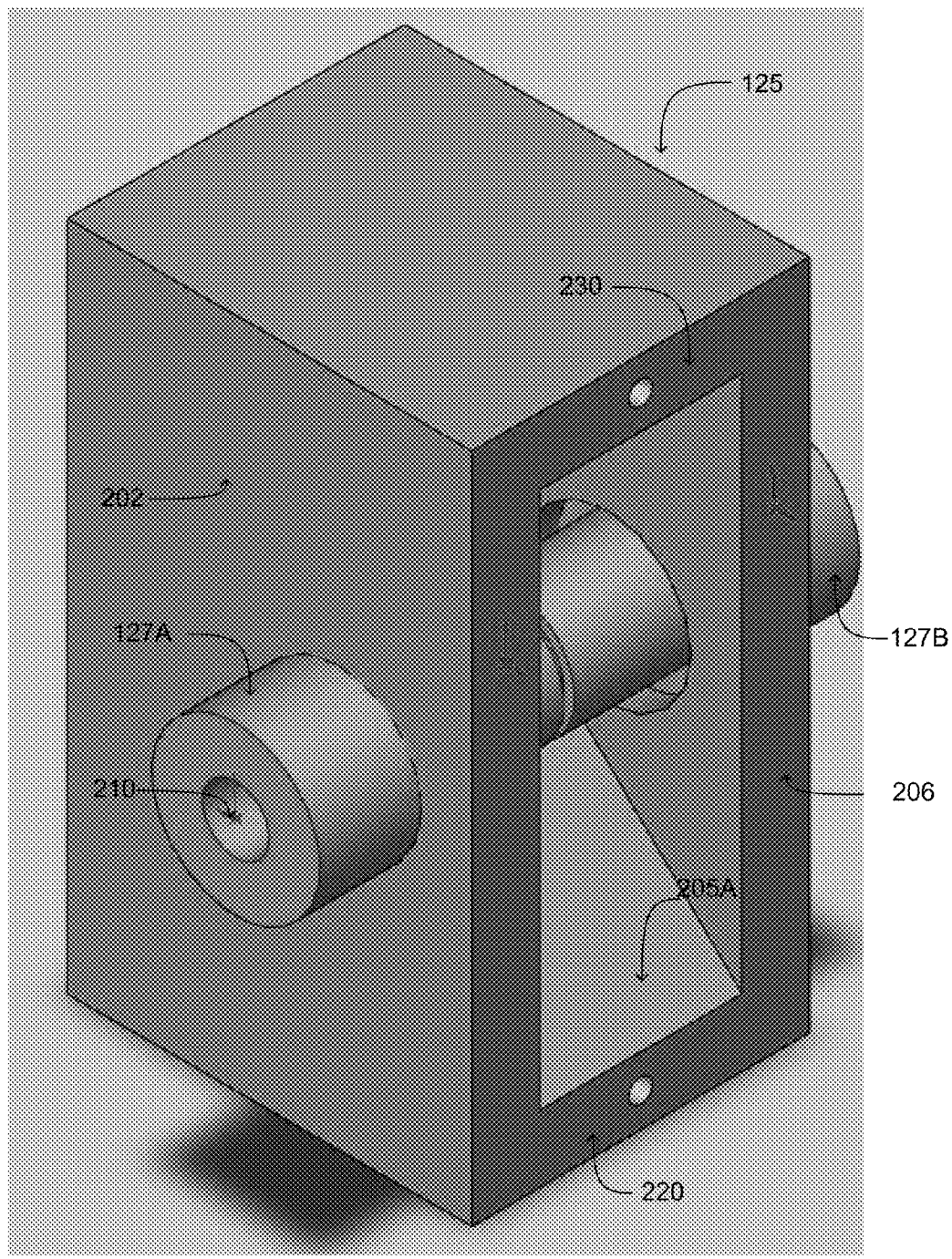
FIG. 2 is an isometric view of one embodiment of a sample measurement chamber.
Figure 3:
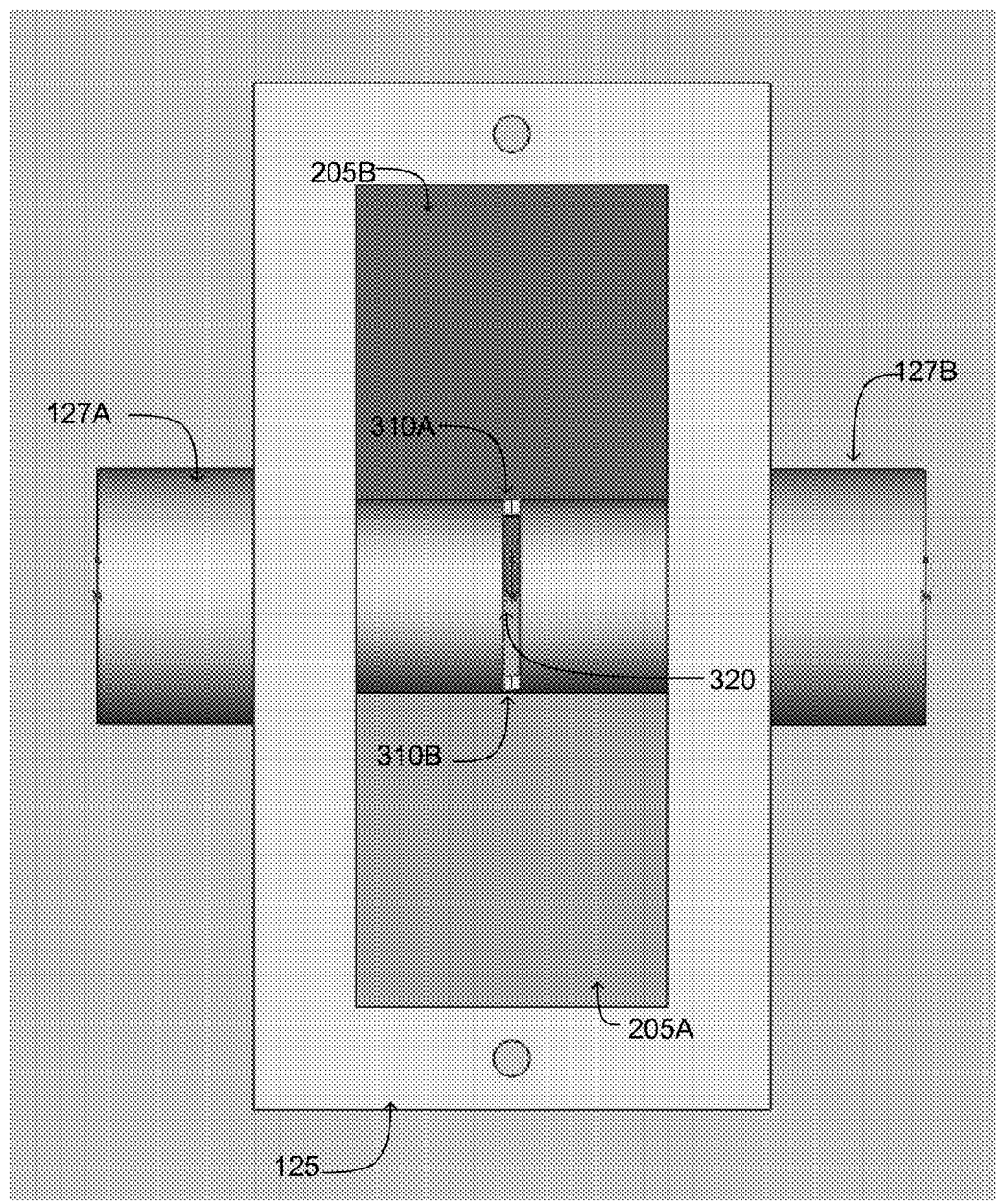
FIG. 3 is a front view of one embodiment of a sample measurement chamber.

A sample measurement chamber 125, further described below in conjunction with FIGS. 2 and 3, is coupled to the mixing chamber 110 through a channel 120. For purposes of illustration, FIG. 1 shows a single sample measurement chamber 125 coupled to the mixing chamber 110, although in other embodiments multiple sample measurement chambers 125 may be coupled to the measurement chamber 110 using different channels 120. Coupling multiple measurement chambers 125 to the mixing chamber 110 allows measurement of different characteristics of the content of the mixing chamber 110. For example, different sample measurement chambers 125 may be used to measure soil pH and/or ultraviolet, visible and near-infrared attenuation by soil using a liquid extractant-soil mixture from the mixing chamber 110 while additional sample measurement chambers 125 measure soil conductivity and/or soil moisture content using the soil itself. In addition to the example measurements described above, a sample measurement chamber 125 may be used to obtain a variety of types of measurements, such as the viscosity of a liquid extractant-soil mixture from the mixing chamber. In one embodiment, the sample measurement chamber 125 receives a portion of the liquid extractant-soil mixture from the mixing chamber 100 and directs light from a light source through portion of the liquid extractant-soil mixture. An optical detector 170 coupled to the sample measurement chamber 125 receives light passing through the portion of the liquid extractant-soil mixture and generates an attenuation spectrum indicating light received by the detector at different wavelengths. The sample measurement chamber 125 is further described below.

One configuration of the sample measurement chamber 125 includes two measurement window holders 127A, 127B which each include a measurement window which have a high transmission of ultraviolet and visible light. However, in other configurations, a sample measurement chamber 125 may include one or more different types of measurement devices 180, which are further described below in conjunction with FIG. 1, allowing different measurement chambers to measure different types of soil characteristics. For example, the measurement window holders 1727A, 127B include quartz or fused-silica windows. In one embodiment, the measurement windows include a hydrophilic film, such as a film of silicon dioxide, to reduce the likelihood of air bubbles developing near the measurement windows, alternatively the measurement window are made from a hydrophilic material. Ultraviolet, visible and near-infrared light passes from a light source 160 to the first window holder 127A, where the light passes through the measurement window and into the sample measurement chamber 125. In one embodiment, the light source 160 comprises a dual ultraviolet-visible/near-infrared light bulb, such as a dual tungsten-deuterium bulb. The light source 160 allows independent control of the production of ultraviolet light and visible light and near-infrared light; for example, modification of a tungsten filament in the light source 160 modifies production of light having wavelengths of 320 nanometers or longer ("visible light" and "near-infrared light") while modification of a deuterium filament in the light source 160 modifies production of light having wavelengths shorter than 400 nanometers ("ultraviolet light" or "UV light").

Light from the measurement window in the first measurement window holder 127A passes through a solution from the mixing chamber 110 entering the sample measurement chamber 125 through the channel 120 and flowing through a separation between the first measurement window holder 127A and the second measurement window holder 127B. For example, a liquid extractant-soil mixture produced in the mixing chamber 110 flows through the separation between the first measurement window holder 127A and the second measurement window holder 127B. The solution from the mixing chamber 110 absorbs a portion of the light from the light source, and the remaining light passes through a second measurement window held by the second measurement window holder 127B.

An optical detector 170 coupled to the second measurement window holder 127B measures the attenuation of the light passing through the solution from the mixing chamber as a function of wavelength. In one embodiment, the optical detector 170 is a spectrometer having a 1 to 4 nanometer resolution. The optical detector 170 has a sufficient sensitivity to allow detection of light passing through materials having a high absorbance. This allows the optical detector 170 to determine an attenuation spectrum associated with solution from the mixing chamber 110 by determining how different wavelengths of light are attenuated by the solution from the mixing chamber 110. Determining the attenuation of a sample at different wavelengths allows more accurate identification of the constituent components of a sample.

Peaks in the attenuation spectrum allow identification of components of the soil, or other sample. For example, attenuation peaks at wavelengths of approximately 200 nanometers and 300 nanometers indicate nitrate-nitrogen in the soil. Similarly, attenuation peaks at wavelengths of approximately 210 nanometers, 230 nanometers and wavelengths from 250-300 nanometers may be used to identify nitrite-nitrogen, bisulfide and organic carbon, respectively, in the soil. Other peaks in the attenuation spectrum may also be used to identify additional components of the soil. Additional peaks of the attenuation spectrum may also be identified and used to determine other components of the soil. Additionally, if the mixing chamber 110 combines additional chemicals with soil and extractant, additional attributes of the soil in a sample may be determined from the effect of the additional chemicals on the attenuation spectrum. For example, if the mixing chamber 110 mixes a pH indicator with soil and extractant, data captured by the optical detector 170 may be used to monitor the pH indicator and ascertain soil pH. As another example, the mixing chamber 110 may mix acids and/or reagents with soil and an extractant to enable a measurement chamber 125 to measure the amount of phosphorous or potassium in the soil.

One or more additional measurement devices 180 may be coupled to the mixing chamber 110 to determine additional data about the liquid extractant-soil mixture produced by the mixing chamber. The one or more additional measurement devices 180 may determine a moisture content of a soil sample, a viscosity of the liquid extractant-soil mixture, soil pH, the temperature of the liquid extractant-soil mixture or any other suitable characteristics of the soil sample or of the generated liquid extractant-soil mixture. The data determined by the additional measurement devices 180 may be combined with the attenuation spectrum determined by the optical detector 170 to increase the accuracy of nutrient identification in the soil sample.

For example, determining the moisture content of the soil sample allows improvement of a nitrate-nitrogen measurement by subtracting the weight of moisture in the soil sample from the weight of the soil sample. Additionally, the type of soil in a soil sample, or the viscosity of the liquid extractant-soil mixture In one embodiment, an additional measurement device 180 is an optical measurement device included in the sample measurement chamber 125 which measures ultraviolet, visible, and near-infrared light from the light source 180 scattered by a portion of the liquid extractant-soil mixture in the sample measurement chamber 125 enabling analysis of the attenuation spectrum to account for errors introduced by particulates in the liquid extractant-soil mixture. In an additional embodiment, a measurement device 180 captures optical reflectivity measurements of the soil in the mixing chamber 110, before extractant mixing, in the UV, visible, near IR and/or mid IR spectra. The reflectivity of dry soil as a function of wavelength is generally correlated to soil type. Such information can be used, in conjunction with the other embodiments discussed herein to provide data about soil characteristics or to refine the measurement of soil characteristics in the sample measurement chamber 125.

By coupling the sample measurement chamber 125 to the mixing chamber 110, the soil analysis device 100 allows for real-time analysis of soil components by integrating mixing of a soil sample and extractant and analysis of the resulting liquid extractant-soil sample. For example, the soil measurement of interest is often a final value after all relevant nutrients in the soil have been extracted into the extractant-soil mixture, which may take a significant amount of time. By integrating a high-speed measurement (typically less than 1 second per measurement) apparatus, such as the optical detector 170 coupled to the sample measurement chamber 125, the measurement can be done many times as the nutrient is being extracted, allowing the final value of the nutrient to be accurately extrapolated in a much shorter amount of time. In contrast, conventional techniques of soil measurement are time-intensive because they rely on discrete steps of preprocessing the soil, extracting nutrients and then measuring nutrients, preventing these conventional methods from obtaining multiple measurements of soil characteristics during the measurement process.

FIG. 2 is an isometric view of one embodiment of a sample measurement chamber 125. In the embodiment of FIG. 2, a first surface 202 of the sample measurement chamber 125 has a first orientation and includes the first measurement window holder 127A while a second surface 206 having the first orientation includes the second measurement window holder 127B. For example, the first surface 202 and the second surface 206 are vertically oriented. In one embodiment, the first measurement window holder 127A and the second measurement window holder 127B have cylindrical cross-sections, although in other embodiments the measurement window holders 127A, 127B have different cross-sectional geometries. Each measurement window holders 127A, 127B includes an opening 210 enabling the coupling of light either by an optical fiber or by free-space optics to a measurement window holder 127. For example, an optical fiber inserted into an opening 210 included in the first measurement window holder directs light from a light source 160 to a first measurement window held by the first measurement window holder 127A and an optical fiber inserted into an opening 210 included in the second measurement window holder 127B directs light passing through a second measurement window included in the second measurement window holder 127B to an optical detector 160.

The sample measurement chamber 125 also includes a first angled surface 205A which contacts a third surface 220, having a second orientation that is perpendicular to the first orientation. For example, if the first surface 202 and the second surface 206 are vertically oriented, the third surface 220 is horizontally oriented. In one embodiment, the angled surface 205 contacts the third surface 220 at an angle. This causes the first angled surface 205A to have a slope which directs particulates entering the sample measurement chamber 125 away from the measurement windows. For example, the first angled surface 205A forms a triangular recession within the sample measurement chamber 125 which directs particulates entering the sample measurement chamber 125 back into the mixing chamber 110. This prevents particles from blocking a sample from flowing between the first measurement window and the second measurement window.

Additionally, the sample measurement chamber 125 may also include a second angled surface 205B, identified in FIG. 3, which contacts a fourth surface 230 that is parallel to the third surface 220 and also has the second orientation perpendicular to the first orientation. For example, if the first surface 202 and the second surface 206 are vertically oriented, the fourth surface 230 is horizontally oriented. The second angled surface 205B contacts the fourth surface 230 at an angle, causing the second angled surface 205B to have a slope which directs air bubbles entering the chamber towards the fourth surface 230. This allows the second angled surface 205B to direct air bubbles back into the mixing chamber 110 rather than settle between the first measurement window holder 127A and the second measurement window holder 128B.

As shown in the front view of one embodiment of a sample measurement chamber 125, the first measurement window holder 127A and the second measurement window holder 127B each include a set of spacers 310A, 310B. For example, the first measurement window holder 127A and the second measurement window holder each include two spacers 127B. In one embodiment, a spacer 310 comprises a rectangular region having flat surfaces and a predetermined height. The height of the spacers 310A, 310B determines a spacing of an attenuation cell 320 comprising an opening between the first measurement window and the second measurement window. Because the optical path length determines the distance in which light travels from the first measurement window to the second measurement window, the optical path length affects the amount of light captured by an optical detector 170 coupled to the second measurement window holder 127B. Thus, modifying the height of one or more spacers 310A, 310B modifies the length of the attenuation cell 320, affecting the amount of visible or ultraviolet light absorbed by a sample from the mixing chamber 110. Precisely specifying the height of the spacers 310A, 310B allows precise definition of the width of the attenuation cell 320. For example, the spacers 310A, 320B included on the first measurement window holder 127A and on the second measurement window holder 127B have heights of 0.5 millimeters, so that when the measurement window holders 127 are inserted into the sample measurement chamber 125, the spacers 310A, 310B included on the first measurement window holder 127A and the spacers 310A, 310B included on the second measurement window holder 127B contact each other to form an attenuation cell 320 having a width of 1 millimeter. However, in other embodiments, other techniques may be used to specify the width of the attenuation cell 320. For example, the length of the window holders 127 may be specified along with the distance between the mounting points of each window holder 127A, 127B in the measurement cell 125 to control the width of the optical path of the attenuation cell 320.

Because the spacers 310A, 310B maintain a fixed distance between the measurement window holders 127, samples of the extractant-soil mixture from the mixing chamber 110 are able to freely flow through the attenuation cell 320. Additionally, the angled surface 205 directs particles from the mixing chamber 110 away from the attenuation cell 320 and also directs air bubbles away from the attenuation cell 320, improving the accuracy of the measured attenuation spectrum by allowing the extractant-soil mixture to flow through the attenuation cell 320 unobstructed. Hence, the spacers 310A allow the sample measurement chamber 125 to include an attenuation cell 320 having a short optical path length while allowing a sample to freely flow through the attenuation cell 320.

Measurement of Soil Composition

Figure 4:
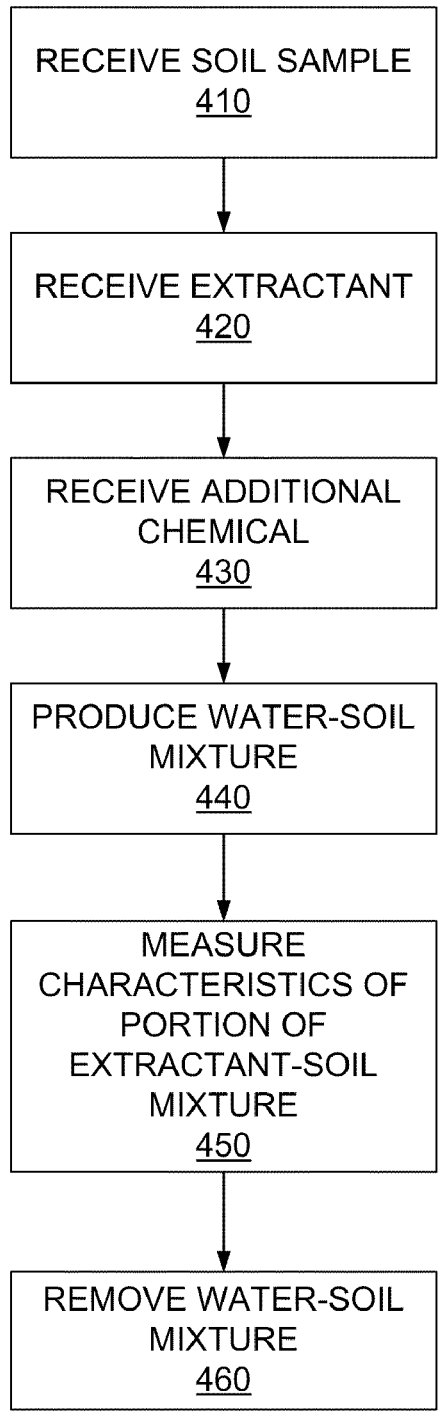
FIG. 4 is a flow chart of one embodiment of a method for measuring data describing soil composition.

FIG. 4 is a flow chart of one embodiment of a method 400 for measuring data describing soil composition. In the embodiment shown by FIG. 4, the mixing chamber 110 initially receives 410 a soil sample having a predetermined weight through the first port 130 or the second port 140. The mixing chamber 110 then receives 420 extractant through the first port 130 or the second port 140. In one embodiment, a predetermined volume or weight of extractant is received 420 based on the weight of the soil sample to provide a predetermined ratio of soil to extractant. However, in an alternate embodiment, the mixing chamber 110 may receive 420 extractant and subsequently receive 410 the soil sample.

In one embodiment, the mixing chamber 110 also receives 430 one or more additional chemicals through the first port 130 or the second port 140. For example, the mixing chamber 110 receives 430 a soil extractant and/or a pH indicator. However, in other embodiments, additional chemicals are not received 430, so the mixing chamber 110 may include the soil and sample and extractant. The contents of the mixing chamber 110 are then mixed to produce a 440 liquid extractant-soil mixture. For example, a motor 115 moves a mixing shaft 115 inside of the mixing chamber 110, and movement of the mixing shaft 115 agitates the soil, extractant and/or chemicals in the mixing chamber 110 to produce 440 a liquid extractant-soil mixture as the soil, extractant and/or chemicals are mixed together by the agitation. In one embodiment, the mixing shaft 115 agitates the soil, extractant and/or chemicals for a predetermined length of time or mixes soil, extractant and/or chemicals until receiving a control signal from an external controller.

A portion of the liquid extractant-soil mixture flows from the mixing chamber 110 through the channel 120 and into a sample measurement chamber 125. The sample measurement chamber 125 is constructed as described above in conjunction with FIGS. 2 and 3 so that an attenuation cell 320 having a short optical path is formed and large particles in the portion are directed away from the attenuation cell 320 by an angled surface 205. In one embodiment, the sample measurement chamber 125 includes a first angled surface 205A and a second angled surface 205B, where the first angled surface 205A directs large particles in the portion of the liquid extractant-soil mixture away from the attenuation cell 320 while the second angled surface 205A directs air bubbles in the portion of the liquid extractant-soil mixture away from the attenuation cell 320. Additionally, in one embodiment, the sample passes through a filter included in the channel 120 to prevent soil particulates, or other large particles, in the sample from entering the attenuation cell 320 in the sample measurement chamber 125. In other embodiments, ultrasonic waves from a source are applied to the liquid extractant-soil mixture in the mixing chamber to reduce the amount of particulates in the liquid extractant-soil mixture by breaking up soil in the liquid extractant-soil mixture or centrifugal force is applied to the liquid extractant-soil mixture to separate particulates from fluid material.

Once in the sample measurement chamber 125, the portion flows through the attenuation cell 320, which is located in a region between a first measurement window and a second measurement window. Ultraviolet, visible, and near-infrared light from a light source 160 coupled to a first measurement window holder 127A passes through the first measurement window, and a portion of the ultraviolet and visible light is absorbed by the portion. The unabsorbed light passes through the sample and through the second measurement window, where it is received by an optical detector 170 coupled to a second measurement window holder 127B which includes the second measurement window. The optical detector 170 generates an attenuation spectrum to measure 450 how the portion absorbs different wavelengths of light. Peaks in the attenuation spectrum associated with the portion allow identification of nutrients, or other components, in the soil sample. Because the soil analysis device 100 includes both the mixing chamber 110 and the sample measurement chamber 125, soil samples may be processed and nutrients in the soil sample may be identified in real-time from the associated attenuation spectrum.

In one embodiment, additional measurement devices 180 included in the mixing chamber 110 also receive portions of the liquid extractant-soil mixture and measure 450 additional characteristics of the soil or characteristics of the extractant-soil mixture. Determination of additional soil or extractant-soil mixture characteristics is further described below in conjunction with FIG. 5, which provides examples of additional characteristics that may be determined. After measuring 450 characteristics of one or more portions of the extractant-soil mixture and determining the composition of the soil, such as nutrients included in the soil, the extractant-soil mixture is removed 460 from the mixing chamber 110 and from the measurement chamber 110. For example, an outlet port 150 of the mixing chamber is opened, allowing the liquid extractant-soil mixture to drain out of the mixing chamber 110. The outlet port 150 may be manually opened or may be automatically opened at a specified time or in response to receiving a control signal.

Figure 5:
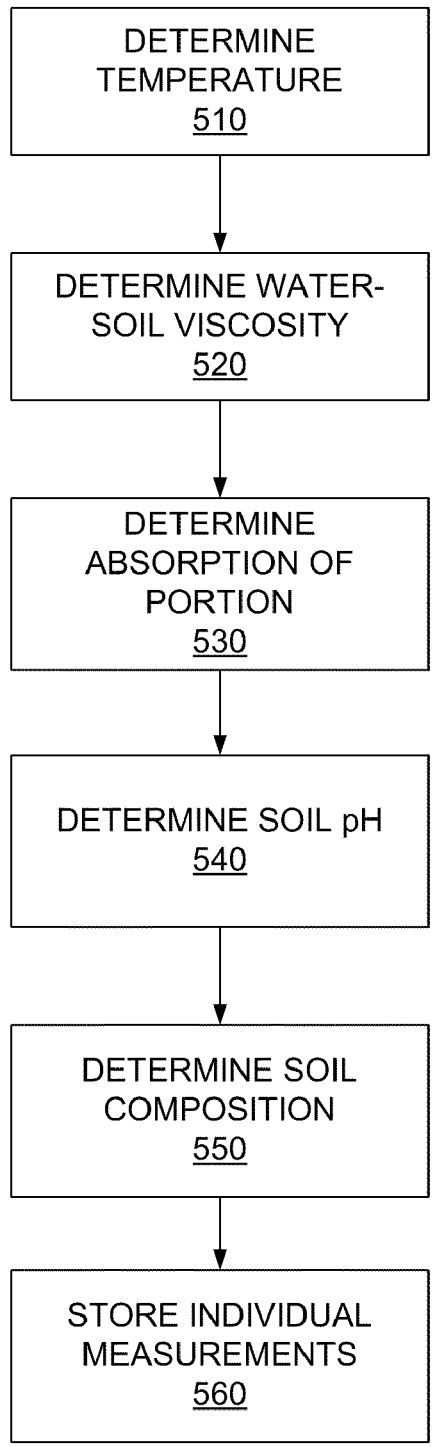
FIG. 5 is a flow chart of one embodiment of a method for capturing multiple types of measurements to determine soil composition.

FIG. 5 is a flow chart of one embodiment of a method for measuring 450 multiple characteristics of a portion of a liquid extractant-soil mixture to determine soil composition. In one embodiment, one or more additional measurement devices 180 are coupled to the mixing chamber 110 and measure 450 various characteristics of portions of a liquid extractant-soil mixture.

In one embodiment, a thermal measurement device 180 determines 510 a temperature of a portion of the liquid extractant-soil mixture and a power detector determines 520 a viscosity of the liquid extractant-soil mixture by measuring the power consumed by the motor 115 to reach a specified speed, or the power consumed by the speed of the motor when a fixed amount of power is applied to the motor 115. In addition to the characteristics determined 510, 520 by the additional measurement devices 180, a portion of the liquid extractant-soil mixture flows through the attenuation cell 320 in the sample measurement chamber 125, where an optical detector 170 determines 530 an attenuation spectrum of the portion of the liquid extractant-soil mixture using ultraviolet, visible, and near-infrared light at different wavelengths from a light source 160, as described above. In one embodiment an additional measurement device 180 may determine the pH of the soil.

The temperature, viscosity, attenuation spectrum and pH are then used to determine 550 the composition of the soil used to produce the liquid extractant-soil mixture. For example, the temperature, viscosity, attenuation spectrum and pH are communicated from the one or more measurement devices 180 and the optical detector 170 to a processor or computing device which determines 550 nutrients included in the soil sample. Additionally, the individual measurements may also be stored 560 or displayed to provide additional information about the soil sample.

Hence, the disclosed soil analysis device 100 improves the accuracy of identifying nutrients in a soil sample while also increasing the speed with which the nutrients included in a soil sample are identified. Coupling one or more measurement devices 180 and one or more sample measurement chambers 125 to the mixing chamber 110 of the soil analysis device 110 to measure multiple characteristics of a soil sample, cross-interferences between measurements may be mitigated, further increasing the accuracy of soil component identification.

Additional Considerations

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a method for automatically identifying characteristics of the composition of a soil sample through the disclosed principles herein. Thus, while particular embodiments and applications have been illustrated and described, it is to be understood that the present invention is not limited to the precise construction and components disclosed herein and that various modifications, changes and variations which will be apparent to those skilled in the art may be made in the arrangement, operation and details of the method and apparatus of the present invention disclosed herein without departing from the spirit and scope of the invention as defined in the appended claims.

What is claimed is:

1. A measurement chamber for determining a characteristic of a liquid extractant-soil mixture, the measurement chamber comprising:
   a first surface having a first orientation, the first surface including a first measurement window holder including a first measurement window allowing transmission of at least ultraviolet light;
   a second surface having the first orientation, the second surface having a second measurement window holder including a second measurement window allowing transmission of at least ultraviolet light, the second measurement window having a specified distance from the first measurement window; and
   a third surface having a second orientation perpendicular to the first orientation, the third surface coupled to the first surface and to the second surface; and
   a first angular surface coupled to the third surface in an orientation which directs particles away from the separation between the first measurement window and the second measurement window.

2. The measurement chamber of claim 1, further comprising:
   a fourth surface having the second orientation, the fourth surface coupled to the first surface and to the second surface and the fourth surface parallel to the third surface; and
   a second angular surface coupled to the fourth surface in an orientation which directs air bubbles away from the separation between the first measurement window and the second measurement window.

3. The measurement chamber of claim 1, wherein the first measurement window and the second measurement window comprise quartz or fused silica windows.

4. The measurement chamber of claim 1, wherein the first measurement window and the second measurement window include a hydrophilic film.

5. The measurement chamber of claim 1, further comprising:
   an optical detector coupled to the second measurement window holder, the optical detector configured to measure ultraviolet light scattered within the separation between the first measurement window and the second measurement window.

6. The measurement chamber of claim 1 coupled to a light source so that light propagating from the light source is attenuated by the liquid extractant-soil mixture and measured by an optical detector coupled to the measurement chamber, the optical detector generating an attenuation spectrum indicating light received by the detector at different wavelengths.

7. The measurement chamber of claim 6, wherein the measurement chamber receives light from the light source through the first measurement window and the optical detector is coupled to the measurement chamber via the second measurement window.

8. The measurement chamber of claim 1, wherein the characteristic of the liquid extractant-soil mixture comprises one or more of: a viscosity of the liquid extractant-soil mixture, a pH of the liquid extractant-soil mixture, a temperature of the liquid extractant-soil mixture, a moisture content of the soil in the liquid extractant soil-mixture, a conductivity of the soil in the liquid extractant-soil mixture, and a reflection spectrum of the soil in the liquid extractant-soil mixture.

9. The measurement chamber of claim 1, wherein the first and second measurement windows allow transmission of visible light.

10. The measurement chamber of claim 1, wherein the first and second measurement windows allow transmission of near-infrared light.

11. A soil analysis device comprising:
a measurement chamber for determining a characteristic of a liquid extractant-soil mixture, the measurement chamber comprising:
a first surface having a first orientation, the first surface including a first measurement window holder including a first measurement window allowing transmission of at least ultraviolet light;
a second surface having the first orientation, the second surface having a second measurement window holder including a second measurement window allowing transmission of at least ultraviolet light, the second measurement window having a specified distance from the first measurement window; and
a third surface having a second orientation perpendicular to the first orientation, the third surface coupled to the first surface and to the second surface; and
a first angular surface coupled to the third surface in an orientation which directs particles away from the separation between the first measurement window and the second measurement window; and
a mixing chamber coupled to the measurement chamber, the mixing chamber configured to receive a soil sample and to receive extractant, the mixing chamber configured to produce and store the liquid soil-extractant mixture by combining the soil sample and the extractant, the mixing chamber configured to transmit the liquid soil-extractant mixture to the measurement chamber.

12. The device of claim 11, wherein the mixing chamber produces the liquid extractant-soil mixture using at least one of: sonication, heating or chemical addition.

13. The device of claim 11, wherein the mixing chamber further comprises:
a motor coupled to a mixing shaft which enters the mixing chamber through an opening and moves responsive to power from the motor so that movement of the mixing chamber combines the soil sample and the extractant to form the liquid extractant-soil mixture.

14. The device of claim 11, wherein the measurement chamber receives the liquid extractant-soil mixture through a channel.

15. The device of claim 14, wherein the channel includes a filter configured to remove particulates from the liquid extractant-soil mixture prior to the measurement chamber receiving the liquid extractant-soil mixture.

16. The device of claim 11, wherein the mixing chamber is configured to apply centrifugal force to the liquid extractant-soil mixture prior to the measurement chamber receiving the liquid extractant-soil mixture.

17. A measurement chamber for determining a characteristic of a liquid extractant-soil mixture, the measurement chamber comprising:
a first surface having a first orientation, the first surface including a first measurement window holder including a first measurement window allowing transmission of at least visible light;
a second surface having the first orientation, the second surface having a second measurement window holder including a second measurement window allowing transmission of at least visible light, the second measurement window having a specified distance from the first measurement window; and
a third surface having a second orientation perpendicular to the first orientation, the third surface coupled to the first surface and to the second surface; and
a first angular surface coupled to the third surface in an orientation which directs particles away from the separation between the first measurement window and the second measurement window.

18. The measurement chamber of claim 17, further comprising:
an optical detector coupled to the second measurement window holder, the optical detector configured to measure visible light scattered within the separation between the first measurement window and the second measurement window.

19. A measurement chamber for determining a characteristic of a liquid extractant-soil mixture, the measurement chamber comprising:
a first surface having a first orientation, the first surface including a first measurement window holder including a first measurement window allowing transmission of at least near-infrared light;
a second surface having the first orientation, the second surface having a second measurement window holder including a second measurement window allowing transmission of at least near-infrared light, the second measurement window having a specified distance from the first measurement window; and
a third surface having a second orientation perpendicular to the first orientation, the third surface coupled to the first surface and to the second surface; and
a first angular surface coupled to the third surface in an orientation which directs particles away from the separation between the first measurement window and the second measurement window.

20. The measurement chamber of claim 19, further comprising:
an optical detector coupled to the second measurement window holder, the optical detector configured to measure near-infrared light scattered within the separation between the first measurement window and the second measurement window.

* * * * *